United States Patent
Häfner et al.

(10) Patent No.: US 6,436,970 B1
(45) Date of Patent: Aug. 20, 2002

(54) COMPOSITIONS FOR THE TREATMENT OF ARDS OR IRDS CONTAINING 3-(CYCLOPROPLYMETHOXY)-N-(3,5-DICHLORO-4-PYRIDINYL)-4-(DIFLUOROMETHOXY) BENZAMIDE AND LUNG SURFACTANT

(75) Inventors: Dietrich Häfner; Klaus Eistetter, both of Constance (DE)

(73) Assignee: Byk Gulden Lomberg Chemische Febrik GmbH, Constance (DE)

( * ) Notice: Subject to any disclaimer, the term of this patent is extended or adjusted under 35 U.S.C. 154(b) by 0 days.

(21) Appl. No.: 09/369,455

(22) Filed: Aug. 6, 1999

Related U.S. Application Data

(63) Continuation of application No. PCT/EP98/00847, filed on Feb. 14, 1998.

(30) Foreign Application Priority Data

Feb. 17, 1997 (DE) .......... 197 05 924
Feb. 19, 1997 (EP) .......... 97102639

(51) Int. Cl.[7] .................. A61K 31/44
(52) U.S. Cl. ................ 514/352; 514/2
(58) Field of Search .......... 514/352, 2; 424/489

(56) References Cited

U.S. PATENT DOCUMENTS

| | | | | |
|---|---|---|---|---|
| 4,223,040 A | * | 9/1980 | Carroll | 424/318 |
| 4,397,839 A | * | 8/1983 | Tanaka | 424/95 |
| 5,712,298 A | * | 1/1998 | Amschler | 514/352 |
| 5,856,196 A | * | 1/1999 | Alvarez | 436/71 |

FOREIGN PATENT DOCUMENTS

| | | | | |
|---|---|---|---|---|
| EP | 0 055 041 | 6/1982 | .......... | A61K/45/08 |
| EP | 0 451 215 | 8/1994 | .......... | A61K/9/127 |
| WO | WO 95/20578 | 8/1994 | .......... | C07D/213/75 |

OTHER PUBLICATIONS

Okuyama, Arch. Biochem. Biophys vol. 221, pp. 99–107, 1983.*

Tanaka, Chem. Abstr. 100, 81529 h, 1984.*

* cited by examiner

*Primary Examiner*—Christopher S. F. Low
*Assistant Examiner*—David Lukton
(74) *Attorney, Agent, or Firm*—Jacobson Holman, PLLC

(57) ABSTRACT

Compositions for treating IRDS and ARDS contain N-(3,5-dichloropyrid-4-yl)3-cyclopropylmethoxy-4-difluoromethoxybenzamide and/or a pharmacologically tolerable salt thereof and lung surfactant.

11 Claims, No Drawings

COMPOSITIONS FOR THE TREATMENT OF ARDS OR IRDS CONTAINING 3-(CYCLOPROPLYMETHOXY)-N-(3,5-DICHLORO-4-PYRIDINYL)-4-(DIFLUOROMETHOXY) BENZAMIDE AND LUNG SURFACTANT

RELATED APPLICATION

This application is a continuation application of application Ser. No. PCT/EP98/00847, filed Feb. 14, 1998, which is pending and for which U.S.A. is a designated country.

TECHNICAL FIELD

The invention relates to a novel composition for the treatment of disease conditions which are designated as Infant Respiratory Distress Syndrome (IRDS) and Acute or Adult Respiratory Distress Syndrome (ARDS).

PRIOR ART

Adult Respiratory Distress Syndrome (ARDS) is a descriptive expression which is applied to a large number of acute, diffuse infiltrative pulmonary lesions of differing etiology if they are associated with a severe gas exchange disorder (in particular arterial hypoxemia). The expression ARDS is used because of the numerous clinical and pathological features common with Infant Respiratory Distress Syndrome (IRDS). If, in the case of IRDS, the lung surfactant deficiency caused by premature birth is predominant, then in the case of ARDS a lung surfactant malfunction is caused by the lung condition based on differing etiologies.

Triggering causes for ARDS can, for example, be (cited in accordance with Harrison's Principles of Internal Medicine 10th Ed. 1983 McGraw-Hill Int. Book Comp.) diffuse pulmonary infections (e.g. due to viruses, bacteria, fungi), aspiration of, for example, gastric juice or in the case of near-drowning, inhalation of toxins or irritants (e.g. chlorine gas, nitrogen oxides, smoke), direct or indirect trauma (e.g. multiple fractures or pulmonary contusion), systemic reactions to inflammations outside the lung (e.g. hemorrhagic pancreatitis, gram-negative septicemia), transfusions of high blood volumes or alternatively after cardiopulmonary bypass.

With a mortality of 50–60% (survey in Schuster Chest 1995, 107:1721–26), the prognoses of an ARDS patient are still to be designated as unfavorable.

The therapy of ARDS consists mainly in the earliest possible application of different forms of ventilation [e.g. PEEP (positive end-expiratory pressure), raising of the oxygen concentration of the respiratory air, SIMV (Synchronized Intermittent Mandatory Ventilation; Harrison's Principles of Internal Medicine 10th Ed 1983 McGraw-Hill Int. Book Comp)] up to extracorporeal membrane oxygenation (ECMO; Zapol and Lemaire Adult Respiratory Distress Syndrome, Marcel Dekker Inc. 1991).

The specific use of various ventilation techniques has only led to a small lowering of mortality and includes the risk of setting in motion a vicious circle. By ventilation with pressure and high $FiO_2$ (Fraction of Inspired Oxygen; proportion of oxygen in the respiratory air), the lungs themselves can be damaged and as a result of this even higher pressures and higher $FiO_2$ may be required in order to obtain an adequate oxygenation of the blood.

Nowadays different pharmacological approaches to the solution are also followed. These include lung surfactant substitution [survey, for example B. Lachmann, D. Gommers and E. P. Eijking: Exogenous surfactant therapy in adults, Atemw.-Lungenkrkh. 1993, 19:581–91; T. J. Gregory et al.: Survanta supplementation in patients with acute respiratory distress syndrome (ARDS), Am. J. Respir. Crit. Care Med. 1994, 149:A567] up to purely antiinflammatory therapy with, for example, prostaglandin $E_1$ ($PGE_1$; Abraham et al. Crit Care Med 1996, 24:10–15) or glucocorticosteroids (Bernard et al. N Engl J Med 1987, 317:1565–70). Although specific successes were achieved by the administration of lung surfactant (e.g. Walmrath et al. Am J Resp Crit Care Med 1996, 154:57–62), the purely antiinflammatory therapies led to few to no successes. This is in direct contrast to the pathological or histopathological findings in ARDS. Thus massive polymorphonuclear leucocyte infiltrations (survey, for example Thiel et al. Anesthesist 1996, 45:113–130) were found in the lungs and the lavage of patients with ARDS and a number of inflammatory mediators are detectable. In testing, $PGE_1$ is additionally present in a liposomal intravenous administration form (Abraham et al. Crit Care Med 1996, 24:10–15) as well as substances which aim at the inhibition of phosphatidic acids (e.g. Lisofylline; Rice et al. Proc Natl Acad Sci 1994, 91:3857–61) or recombinant human interleukin 1 (IL-1) receptor antagonists (Fisher et al. JAMA 1994, 271:1836–43). Both PGE, and the IL-1 receptor antagonist, however, are restricted in their therapeutic utility by side effects.

WO96/09831 indicates compositions for the treatment of ARDS and IRDS which contain a glucocorticosteroid and lung surfactant. EP-B-0 451 215 describes compositions for the administration of a pharmaceutical active compound via the lungs. These compositions include liposomes which contain a pharmaceutical active compound and a lung surfactant protein. These systems are also proposed for the treatment of ARDS and IRDS. EP-B-0 055 041 describes preparations for inhalation or infusion for the treatment of disorders of the respiratory organs, which contain an active compound against disorders of the respiratory organs and natural lung surfactant. Compositions for the treatment of ARDS and IRDS are not disclosed.

DESCRIPTION OF THE INVENTION

It has now surprisingly been found that by the administration of a combination of N-(3,5-dichloropyrid-4-yl)-3-cyclopropylmethoxy-4-difluoromethoxybenzamide and lung surfactant a synergistic effect can be achieved in the treatment of IRDS and ARDS.

The invention therefore relates to a composition for the treatment of IRDS and ARDS comprising N-(3,5-dichloropyrid-4-yl)-3-cyclopropylmethoxy-4-difluoromethoxybenzamide and/or its pharmacologically tolerable salts and lung surfactant.

Further embodiments of the invention follow from the Patent Claims.

The preparation of N-(3,5-dichloropyrid-4-yl)-3-cyclopropylmethoxy-4-difluoromethoxybenzamide and use as a phosphodiesterase (PDE) IV inhibitor is described in WO95/01338. Pharmacologically tolerable salts of N-(3,5-dichloropyrid-4-yl)-3-cyclopropylmethoxy-4-difluoromethoxybenzamide which may be mentioned, for example, are water-soluble and water-insoluble acid addition salts with acids such as, for example, hydrochloric acid, hydrobromic acid, phosphoric acid, nitric acid, sulfuric acid, acetic acid, citric acid, D-gluconic acid, benzoic acid, 2-(4-hydroxybenzoyl)benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid or 3-hydroxy-2-naphthoic acid, where the acids are employed in the salt preparation—depending on whether it is a mono- or polybasic acid and depending on which salt is desired—in an equimolar quantitative ratio or one differing therefrom.

Lung surfactant is understood according to the invention as meaning the numerous known compositions and their modifications which have the function of natural lung surfactant. Natural lung surfactant has surface-active properties and reduces the surface tension in the alveolar region of the lungs. A simple and rapid quantitative in vitro assay to determine the surface activity of a surfactant preparations is e.g. the Wilhelmy balance [Goerke, J Biochim Biophys Acta, 344:241–261 (1974); King R. J. and Clements J. A., Am J Physiol 223:715–726 (1972)]. It gives an indication of surfactant quality in terms of the ability to approach a surface tension of near zero mN/m. It is performed by injecting a surfactant suspension at defined concentrations of phospholipids into a hydrous solution. The phospholipids spread to the air-liquid phase building a so-called monolayer. This monolayer reduces the surface tension of the hydrous solution. A platinum plate is carefully dipped into the solution. Now the force which pulls down the platinum plate can be measured with sensitive transducers. This force is proportional to the surface tension and depends on the dimensions of the platinum plate. An other method to describe the surface activity of surfactant preparations is the pulsating bubble surfactometer [Possmayer F., Yu S. and Weber M., Prog Resp Res, Ed.v. Wichert, Vol. 18:112–120 (1984)]. The activity of a surfactant preparation can also be assessed by an in vivo assay, for example, as described below in the section Pharmacology. Measurement of lung compliance, blood gases and ventilator pressure will provide indices of activity.

Lung surfactant is to be understood according to the invention preferentially as compositions which will show activity in such an assay. Particular mention may be made of compositions which will show an activity in such an assay similar or greater to that of natural, in particular human, lung surfactant.

In particular lung surfactant compositions comprise phospholipids and inter alia can additionally contain lung surfactant proteins. Further components which may be present in lung surfactant compositions are fatty acids, for example palmitic acid. The lung surfactant compositions may also contain electrolytes such as calcium, magnesium and/or sodium salts to set a favourable viscosity. Commercially available products which may be mentioned are Curosurf® (Serono, Pharma GmbH, Unterschleissheim), a highly purified natural surfactant from homogenized pigs' lungs, Survanta® (Abbott GmbH, Wiesbaden) and Alveofact® (Dr. Karl Thomae GmbH Biberach), both extracts of bovine lungs, and also Exosurf® (Deutsche Wellcome GmbH, Burgwedel), a synthetic phospholipid with auxiliaries. Possible lung surfactant proteins are both the proteins obtained from natural sources, such as, for example, pulmonary lavage or extraction from amniotic fluid, and also the genetically engineered proteins. According to the invention, the lung surfactant proteins designated by SP-B and SP-C and their modified derivatives are particularly of interest. The amino acid sequences of these lung surfactant proteins, their isolation or preparation by genetic engineering are known (e.g. from WO-86/03408, EP-A-0 251, 449, WO-89/04326, WO-87/06943, WO-88/03170, EP-A-0 368 823 and EP-A-0 348 967). Modified derivatives of SP-C which differ from human SP-C by replacement of certain amino acids are disclosed for example in WO91/18015 and WO95/32992. Particular mention may be made of the SP-C derivatives disclosed in WO95/32992. According to the invention a particularly preferred recombinant SP-C derivative [hereinafter referred to as r-SP-C (FF/I)] differs from human SP-C by replacement of the two cysteines in position 4 and 5 by phenylalanine and replacement of the methionine in position 32 by isoleucine. WO95/32992 describes lung surfactant compositions containing 80 to 95% by weight of phospholipids, 0.5 to 3.0 percent by weight of surfactant proteins, 4 to 7% by weight of fatty acid, preferably palmitic acid, and 1 to 3% by weight of calcium chloride. EP-B-0 100 910, EP-A-0 110 498, EP-B-0 119 056, EP-B-0 145 005 and EP-B-0 286 011 describes phospholipid compositions with and without lung surfactant proteins which are suitable, for example, as components of the preparations according to the invention.

The invention further relates to the use of the compositions according to the invention for the production of medicaments which are employed for the treatment and/or prophylaxis of IRDS or ARDS.

The invention furthermore relates to medicaments for the treatment and/or prophylaxis of the illnesses mentioned, which contain the compositions according to the invention.

The compositions according to the invention are made available either in liquid form for intratracheal or intrabronchial administration or in powder form for administration by inhalation. The compositions are prepared by procedures familiar to those skilled in the art, if appropriate using further suitable pharmaceutical auxiliaries. A powder form is obtained, for example, by mixing liquid lung surfactant preparations, e.g. aqueous suspensions, with aqueous suspensions of N-(3,5-dichloropyrid-4-yl)-3-cyclopropylmethoxy-4-difluoromethoxybenzamide and then lyophilizing and micronizing it. Alternatively, a solution of a lung surfactant and N-(3,5-dichloropyrid-4-yl)-3-cyclopropylmethoxy-4-difluorometh-oxybenzamide can be lyophilized in a suitable solvent, such as, for example, tert-butanol, and then micronized. Spray-drying of a mixture of an aqueous lung surfactant suspension and an aqueous N-(3,5-dichloropyrid-4-yl)-3-cyclopropylmethoxy-4-difluoromethoxybenzamide suspension or a solution of a lung surfactant and N-(3,5-dichloropyrid-4-yl)-3-cyclopropylmethoxy-4-difluoromethoxybenzamide in suitable solvents, such as alcohols, (e.g. methanol, ethanol, 2-propanol) chloroform, dichloromethane, acetone and their mixtures, which optionally can additionally contain water also leads to powdered preparations. Administration by inhalation can also be carried out by atomizing solutions or suspensions which contain the compositions according to the invention. Compositions according to the invention advantageously contain 1 to 30 percent by weight of N-(3,5-dichloropyrid-4-yl)-3-cyclopropylmethoxy-4-difluoromethoxybenzamide and 15 to 99 percent by weight of lung surfactant of the dry mass. Such range for lung surfactant in pharmaceutical compositions is suitable according to WO96/09831, which indicates compositions for the treatment of ARDS and IRDS.

Below, the preparation of a powdered preparation by spray-drying is described by way of example.

EXAMPLE 1

8.2 g of 1,2-dipalmitoyl-3-sn-phosphatidylcholine, 3.46 g of 1-palmitoyl-2-oleoyl-3-sn-phosphatidylglycerolammonium, 2.7 g of N-(3,5-dichloropyrid-4-yl)-3-cyclopropylmethoxy-4- difluoromethoxybenzamide, 0.56 g of palmitic acid, 0.3 g of calcium chloride and 0.2 g of r-SP-C (FF/I) are dissolved in 700 ml of 2-propanol/water (90:10) and spray-dried in a Büchi B 191 laboratory spray-dryer. Spray conditions: drying gas nitrogen, inlet temperature 110° C., outlet temperature 59–61° C. A fine, cream-colored powder is obtained.

EXAMPLE 2

8.2 g of 1,2-dipalmitoyl-3-sn-phosphatidylcholine, 3.46 g of 1-palmitoyl-2-oleoyl-3-sn-phosphatidylglycerolammonium, 0.27 g of N-(3,5-dichloropyrid-4-yl)-3-cyclopropylmethoxy4-difluoromethoxybenzamide, 0.56 g of palmitic acid, 0.3 g of calcium chloride and 0.2 g of r-SP-C (FF/I) are spray-dried as described in Example 1.

EXAMPLE 3

8.2 g of 1,2-dipalmitoyl-3-sn-phosphatidylcholine, 3.46 g of 1-palmitoyl-2-oleoyl-3-sn-phosphatidylglycerolammonium, 0.027 g of N-(3,5-dichloropyrid-4-yl)-3-cyclopropylmethoxy-4-difluoromethoxybenzamide, 0.56 g of palmitic acid, 0.3 g of calcium chloride and 0.2 g of r-SP-C (FF/I) are spray-dried as described in Example 1.

EXAMPLE 4

10.0 g of 1,2-dipalmitoyl-3-sn-phosphatidylcholine, 2.6 g of N-(3,5-dichloropyrid-4-yl)-3-cyclopropylmethoxy-4-difluoromethoxybenzamide, 0.74 g of tyloxapol and 1.1 g of 1-hexadecanol are dissolved in 500 ml of 2-propanol/water (90:10) and spray-dried in a Büchi B 191 laboratory spray-dryer. Spray conditions: drying gas nitrogen, inlet temperature 110° C., outlet temperature 58–60° C. A white to off-white powder is obtained.

Below the preparation of a lyophilized composition is described by way of example.

EXAMPLE 5

8.0 g of a purified lung surfactant from bovine lungs and 2.0 g of N-(3,5-dichloropyrid-4-yl)-3-cyclopropylmethoxy-4-difluoromethoxybenzamide are added to 90 ml of water. The suspension obtained is lyophilized at −25° C. to yield a light, off-white, fluffy material.

The invention furthermore relates to a method for the treatment of mammals, including humans, who are suffering from IRDS or ARDS. The method is characterized in that a therapeutically active and pharmacologically tolerable amount of the composition according to the invention is administered to the sick mammal.

The invention further relates to the composition according to the invention for use in the treatment IRDS or ARDS.

The dosage of the active compounds takes place in the order of magnitude customary for N-(3,5-dichloropyrid4-yl)-3-cyclopropylmethoxy-4-difluoromethoxybenzamide and for lung surfactant. The person skilled in the art is familiar with dosages customary for N-(3,5-dichloropyrid-4-yl)-3-cyclopropylmethoxy-4-difluoromethoxybenzamide and lung surfactant. Dosages customary for N-(3,5-dichloropyrid-4-yl)-3-cyclopropylmethoxy-4-difluoromethoxybenzamide are for example described in WO95/01338 and dosages customary for lung surfactant are for example described in EP 0 119 056, EP 0 406 732, WO91/18015 or WO96/09831. The administration of the compositions according to the invention is accomplished according to methods known by those skilled in the art.

Preferably the compositions according to the invention are dissolved or resuspended in a suitable solvent or resuspension medium for administration. This is particularly preferred in case of spray dried or lyophilized compositions. Preferably saline solution is used as suitable resuspension medium. It is suitable to administer (per single administration) suspensions or solutions of the compositions according to the invention which contain from 25 to 100 mg phospholipids and from 0.6 to 6 mg N-(3,5-dichloropyrid-4-yl)-3-cyclopropylmethoxy-4-difluoromethoxybenzamide per kg body weight.

The preparations according to the invention are administered 3 to 4 times daily for 2 to 4 days. For example, preparations comprising 4 mg of N-(3,5-dichloropyrid-4-yl)-3-cyclopropylmethoxy-4-difluoromethoxybenzamide, and 50 mg of phospholipids are administered 6 times at an interval of 6 hours by inhalation or intratracheally or intrabronchially.

PHARMACOLOGY

Adult Sprague Dawley rats are artificially ventilated with pure oxygen and a positive end-expiratory pressure (PEEP; in order to guarantee oxygenation of the rats) and lavaged until their endogenous lung surfactant is washed out (D. Hätfner, U. Kilian and R. Beume: Comparison of four lung surfactant preparations in an animal model of adult respiratory distress syndrome (ARDS). Am. Rev. Respir. Dis. 1993, 147:A719; D. Häfner, P.-G. Germann, D. Hauschke, Pulmonary Pharmacology (1994) 7, 319–332). This is manifested by the fact that in the animals the preliminary values of the arterial oxygen partial pressure ($PaO_2$) of 500–550 mm Hg (in the case of pure oxygen ventilation and PEEP) decrease to values of 50–110 mm Hg. Animals of the control group, which are not treated with lung surfactant, remain with their $PaO_2$ at these low values throughout the observation period. Sixty minutes after the $PaO_2$ has decreased to these values, lung surfactant or lung surfactant together with N-(3,5-dichloropyrid-4-yl)-3-cyclopropylmethoxy-4-difluoromethoxybenzamide is instilled intratracheally. The blood gases are determined 30 and 120 minutes after instillation.

In Table 1 and Table 2 which follow, in line A the average values (standard deviation) of the $PaO_2$ are indicated in mm Hg for the time 30 minutes (constant PEEP of 8 cm $H_2O$) after intratracheal instillation and in line B 120 minutes after intratracheal instillation. It can be seen from Table 1 that the sole administration of N-(3,5-dichloropyrid-4-yl)-3-cyclopropylmethoxy4-difluoromethoxybenzamide has no influence on the $PaO_2$. This follows by comparison with the untreated control animals. The administration of lung surfactant (25 or 100 mg/kg) leads to a rise in the $PaO_2$ (the lung surfactant used corresponds to a composition according to Example I without N-(3,5-dichloropyrid-4-yl)-3-cyclopropylmethoxy-4-difluoromethoxybenzamide). The addition of 600 μg/kg or 6.0 mg/kg of N-(3,5-dichloropyrid-4-yl)-3-cyclopropylmethoxy-4-difluoromethoxybenzamide to the respective lung surfactant dose improves the $PaO_2$ values in comparison with the respective lung surfactant doses. It follows from this that the joint administration of N-(3,5-dichloropyrid-4-yl)-3-cyclopropylmethoxy-4-difluoromethoxybenzamide and lung surfactant leads to an unexpected superadditive action. It is therefore possible to save a part of the very expensive lung surfactant, or else to obtain an increased action of each individual component.

TABLE 1

|   | Control | Compound A* 600 ug/kg | Lung surfactant 25 mg/kg | Lung surfactant 25 mg/kg + Compound A* 600 µg/kg | Lung surfactant 100 mg/kg | Lung surfactant 100 mg/kg + Compound A* 600 µg/kg |
|---|---|---|---|---|---|---|
| A | 67 ± 17 | 59 ± 12 | 305 ± 96 | 341 ± 105 | 427 ± 78 | 473 ± 31 |
| B |  | 75 ± 24 | 311 ± 111 | 359 ± 74 | 457 ± 58 | 478 ± 43 |

*Compound A = N-(3,5-dichloropyrid-4-yl)-3-cyclopropylmethoxy-4-difluoromethoxybenzamide

TABLE 2

|   | Lung surfactant 25 mg/kg | Lung surfactant 25 mg/kg + Compound A* 6.0 mg/kg | Lung surfactant 100 mg/kg | Lung surfactant 100 mg/kg + Compound A* 6.0 mg/kg |
|---|---|---|---|---|
| A | 305 ± 96 | 407 ± 65 | 427 ± 78 | 502 ± 32 |
| B | 311 ± 111 | 369 ± 147 | 457 ± 58 | 511 ± 28 |

*Compound A = N-(3,5-dichloropyrid-4-yl)-3-cyclopropylmethoxy-4-difluoromethoxybenzamide The histological work-ups of the lungs of these animals carried out in connection with the experiment show a strong formation of so-called hyaline membranes (HM) and a strong influx of inflammatory cells [e.g. polymorphonuclear neutrophilic leucocytes (PMNL)] as an expression of the development of an acute respiratory distress syndrome.

In the investigation of preparations according to the invention comprising N-(3,5-dichloropyrid-4-yl)-3-cyclopropylmethoxy-4-difluoromethoxybenzamide and lung surfactant (phospholipid mixture) with or without surfactant proteins in this model, it was found that the oxygenation and the histological changes (inhibition of the formation of HM and inhibition of the influx of PMNL) improve superadditively in comparison with the sole administration of lung surfactant or N-(3,5-dichloropyrid-4-yl)-3-cyclopropylmethoxy-4-difluoromethoxybenzamide. It follows from this that as a result of this unexpected synergistic effect the treatment of IRDS and ARDS can be shortened and the high mortality accompanying these syndromes can be reduced.

What is claimed is:

1. A composition for the treatment of IRDS (Infant Respiratory Distress Syndrome) and ARDS (Adult Respiratory Distress Syndrome) comprising N-(3,5-dichloropyrid-4-yl)-3-cyclopropylmethoxy-4-difluoromethoxybenzamide or a pharmaceutically tolerable salt thereof, together with at least one phospholipid-comprising lung surfactant.

2. The composition as claimed in claim 1, wherein the lung surfactant comprises a mixture of phospholipids.

3. The composition as claimed in claim 2, wherein the phospholipids are those which occur in natural lung surfactant.

4. The composition as claimed in claim 2, wherein the lung surfactant comprises lung surfactant protein.

5. The composition as claimed in claim 4, wherein the lung surfactant protein is a protein selected from the group consisting of SP-B (surfactant protein-B), SP-C (surfactant protein-C) and a modified derivative of either.

6. The composition as claimed in claim 1, wherein the phospholipid-comprising lung surfactant comprises lung surfactant obtained by pulmonary lavage.

7. The composition as claimed in claim 1, wherein the phospholipid-comprising lung surfactant has the function of natural lung surfactant.

8. A composition for the treatment of IRDS (Infant Respiratory Distress Syndrome) or ARDS (Adult Respiratory Distress Syndrome) comprising N-(3,5-dichloropyrid-4-yl)-3-cyclopropylmethoxy-4-difluoromethoxybenzamide or a pharmaceutically tolerable salt thereof, together with a lung surfactant comprising lung surfactant protein.

9. The composition as claimed in claim 8 wherein the lung surfactant protein is a recombinant SP-C (surfactant protein-C) derivative which differs from human SP-C by replacement of the two cysteines (in positions 4 and 5) by phenylalanine and replacement of the methionine in position 32 by isoleucine.

10. The composition as claimed in claim 1, which contains (based on 100 percent by weight) from 1 to 30 percent by weight of N-(3,5-dichloropyrid-4-yl)-3-cyclopropylmethoxy-4-difluoromethoxybenzamide and from 15 to 99 percent by weight of phospholipid-comprising lung surfactant on a dry-mass basis.

11. The composition as claimed in claim 1 in powder form.

* * * * *